United States Patent [19]

Anderson et al.

[11] 4,252,810

[45] Feb. 24, 1981

[54] 9,10-DIHYDRO-4H-BENZO[4,5]CYCLOHEPTA [1,2-b]THIOPHEN-4,9-IMINES

[75] Inventors: Paul S. Anderson; Ben E. Evans, both of Lansdale, Pa.

[73] Assignee: Merck & Co., Inc., Rahway, N.J.

[21] Appl. No.: 960,811

[22] Filed: Nov. 15, 1978

[51] Int. Cl.$^3$ ............... A61K 31/38; A61K 31/44; C07D 495/12
[52] U.S. Cl. .................. 424/256; 544/378; 546/63; 549/43; 549/48
[58] Field of Search ............ 546/63; 424/256

[56] References Cited

U.S. PATENT DOCUMENTS

| | | | |
|---|---|---|---|
| 3,892,756 | 7/1975 | LeReincy et al. | 424/258 |
| 4,064,139 | 12/1977 | Anderson et al. | 260/326.25 |
| 4,123,546 | 10/1978 | Haire | 424/274 |

FOREIGN PATENT DOCUMENTS 2305496  8/1973  Fed. Rep. of Germany ............ 546/63

OTHER PUBLICATIONS

Waldvogel et al., "Helv. Chim. Acta.," vol. 59 (3), 1976, pp. 866–877.
Bastian et al., "Helv. Chim. Acta.," vol. 49 (26), 1966, pp. 214–234.

Primary Examiner—Donald G. Daus
Assistant Examiner—James H. Turnipseed
Attorney, Agent, or Firm—Mario A. Monaco; William H. Nicholson

[57] ABSTRACT

9,10-Dihydro-4H-benzo[4,5]cyclohepta [1,2-b]thiophen-4,9-imines, derivatives and pharmaceutically acceptable salts thereof are useful as antianxiety agents, as muscle relaxants and in the treatment of extrapyramidal disorders such as in Parkinson's disease.

9 Claims, No Drawings

9,10-DIHYDRO-4H-BENZO[4,5]CYCLOHEPTA[1,2-B]THIOPHEN-4,9-IMINES

BACKGROUND OF THE INVENTION

This invention is concerned with novel 9,10-dihydro-4H-benzo[4,5]cyclohepta[1,2-b]thiophen-4,9-imines, derivatives, optical isomers and pharmaceutically acceptable salts thereof which are useful as antianxiety agents, muscle relaxants, and in the treatment of extrapyramidal disorders such as in Parkinson's disease.

Structurally related compounds are known in the art to have qualitatively similar utilities. For example U.S. Pat. No. 3,892,756 discloses 10,11-dihydro-5H-dibenzo[a,d]cyclohepten-5,10-imine and derivatives which are unsubstituted at the 5-bridgehead carbon; and Belgian Pat. No. 829,075 discloses 9,10-dihydroanthracen-9,10-imines and derivatives.

It is an object of this invention to provide the novel compounds, 9,10-dihydro-4H-benzo[4,5]cyclohepta[1,2-b]thiophen-4,9-imines; novel processes for their synthesis; pharmaceutical compositions comprising them as active ingredient; and a novel method of treatment where there is an indicated need for an antianxiety agent, muscle relaxant, or a treatment for extrapyramidal disorders.

DETAILED DESCRIPTION OF THE INVENTION

The novel compounds of this invention have structural formula:

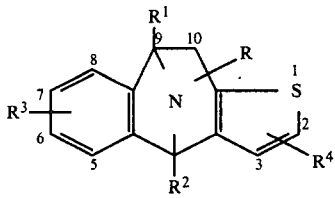

or a pharmaceutically acceptable salt thereof, wherein R is
 (1) hydrogen,
 (2) lower alkyl, especially $C_{1-5}$ alkyl, preferably methyl or ethyl,
 (3) lower alkenyl, especially $C_{2-5}$ alkenyl, preferably vinyl or allyl,
 (4) phenyl(or substituted phenyl)-lower alkyl, especially phenyl(or substituted phenyl)-$C_{1-3}$ alkyl, preferably benzyl or substituted benzyl, wherein the substituent is halo such as fluoro, chloro or bromo, especially chloro, or lower alkyl especially $C_{1-3}$ alkyl,
 (5) lower cycloalkyl, especially $C_{3-6}$ cycloalkyl, preferably cyclopropyl or cyclohexyl,
 (6) lower(cycloalkyl-alkyl), especially $C_{3-6}$ cycloalkyl-$C_{1-3}$ alkyl, or
 (7) di(lower alkyl)amino-lower alkyl, especially dimethylaminopropyl;

$R^1$ is
 (1) hydrogen,
 (2) lower alkyl, especially $C_{1-5}$ alkyl, preferably methyl or ethyl,
 (3) lower alkenyl, especially $C_{2-5}$ alkenyl, preferably vinyl or allyl,
 (4) phenyl-lower alkyl, especially phenyl-$C_{1-3}$ alkyl, preferably benzyl,
 (5) lower cycloalkyl, especially $C_{3-6}$ cycloalkyl, preferably cyclopropyl or cyclohexyl, or
 (6) lower(cycloalkyl-alkyl), especially $C_{3-6}$ cycloalkyl-$C_{1-3}$ alkyl, $R^2$ is
 (1) hydrogen,
 (2) lower alkyl, especially $C_{1-5}$ alkyl, preferably methyl or ethyl,
 (3) lower alkenyl, especially $C_{2-5}$ alkenyl, preferably vinyl or allyl,
 (4) phenyl-lower alkyl, especially phenyl-$C_{1-3}$ alkyl, preferably benzyl,
 (5) lower(cycloalkyl-alkyl), especially $C_{3-6}$ cycloalkyl-$C_{1-3}$ alkyl, or
 (6) di(lower alkyl)amino-lower alkyl, especially dimethylaminopropyl;

$R^3$ and $R^4$ are independently
 (1) hydrogen,
 (2) halogen, such as chloro, bromo, fluoro, or iodo,
 (3) lower alkoxy, especially $C_{1-5}$ alkoxy, preferably methoxy,
 (4) trifluoromethylthio,
 (5) cyano,
 (6) carboxy, or
 (7) hydroxy.

A preferred group of compounds is that wherein $R^1$ is hydrogen.

Another preferred group of compounds is that wherein $R^1$, $R^3$ and $R^4$ are hydrogen.

Where $R^3$ is other than hydrogen, it is preferred that it occupy the 6 or 7 positions of the tricyclic ring system.

The preferred definition for $R^2$ is lower alkyl, especially methyl or ethyl.

Preferred definitions for R are hydrogen, lower alkyl or benzyl.

The novel compounds of this invention wherein R is hydrogen are generally prepared by reduction of the N-hydroxy analog. The preferred reducing agent is nascent hydrogen generated by the action of a metal, preferably zinc with an acid such as acetic acid at 40° to 100° C. for 1 to about 10 hours.

Where R is other than hydrogen, the novel compounds are prepared by alkylation of the compounds wherein R is hydrogen with the appropriate reagent of formula R-halo wherein halo represents chloro, bromo or iodo. The reaction is normally conducted in an inert solvent such as benzene, or toluene. However, the alkylating reagent, depending on its physical properties, may be used in sufficiently excess amount to act as solvent. It is preferred to conduct the reaction in the presence of an acid acceptor such as an inorganic carbonate such as sodium carbonate, an organic base such as pyridine, or a basic resin. Temperatures of about 50° C. to about 100° C. may be employed over reaction times of about 10 hours to about 5 days.

Where R is alkyl or substituted alkyl, the compounds also may be prepared by reduction of an N-acyl compound such as alkoxycarbonyl to give methyl or other alkanoyl groups to provide the other alkyl groups. The preferred reducing system is a metal hydride such as lithium aluminum hydride in an ethereal solvent such as ether, tetrahydrofuran or 1,2-dimethoxyethane or the like. The reaction proceeds satisfactorily at room temperature but temperatures from about 0° C. to about 50° C. are appropriate with reaction times of 10–13 hours.

An additional alkylation method involves the treatment of the imine with an aldehyde and sodium cyanoborohydride (NaCNBH₃) in an ether such as tetrahydrofuran, 1,2-dimethoxyethane or di(2-methoxyethyl)ether, preferably tetrahydrofuran, at about 10°-50° C., preferably 25° C., until the reaction is substantially complete, usually for about 6 hours to about 3 days, preferably 2 days.

Novel compounds having a substituent on the benzene and/or the thiophene ring are generally prepared by metathesis of the appropriate bromo or iodo compound. For example treatment with a sodium lower alkoxide in the presence of copper dust in an inert organic solvent such as dimethyl formamide at 50°-150° C. for 1-10 hours yields the corresponding lower alkoxy compound.

The 6 or 7-hydroxy compounds are prepared from the corresponding alkoxy, preferably methoxy, compounds by de-etherification. The preferred process comprises heating with pyridine hydrochloride at 200°-220° C. for 3-10 hours.

Treatment of a bromo or iodo compound with cuprous cyanide in an inert organic solvent such as dimethyl formamide at reflux temperature for 1-10 hours yields the corresponding cyano compound.

Hydrolysis of the above cyano compounds with a mineral acid such as hydrochloric acid at about 50° to 150° C. and especially at reflux temperature produces the corresponding carboxy substituted compounds.

Also treatment of the bromo or iodo compounds with bis(trifluoromethylthio)mercury and copper dust in an inert organic solvent such as dimethyl formamide or quinoline at about 100°-200° C. for 1-10 hours yields the trifluoromethylthio derivatives.

The novel compounds can be resolved into their optical isomers by standard techniques, such as the formation of diastereomeric pairs by salt formation with an optically active acid, such as (—)di-p-toluoyl-d-tartaric acid and/or (+)-di-p-toluoyl-1-tartaric acid followed by fractional crystallization and regeneration of the free base.

The starting materials and processes used for preparing the intermediates used in the above described processes are fully described in the Examples.

Also included within the scope of the present invention are the non-toxic pharmaceutically acceptable salts of the novel compounds. Acid addition salts of the imine compounds are formed by mixing a solution of the imine with a solution of a pharmaceutically acceptable non-toxic acid such as hydrochloric acid, fumaric acid, maleic acid, succinic acid, acetic acid, citric acid, tartaric acid, phosphoric acid, or the like. Where the novel compound carries a carboxylic acid group, the invention also contemplates sodium, potassium, and calcium salts thereof.

In the method of treatment aspect of the present invention, the novel imines of this invention are capable of producing anxiety relief without causing excessive sedation or sleep at a dosage level of from about 0.01 to about 50 mg per kilogram of body weight preferably about 0.05-10 mg/kg of body weight on a regimen of 1-4 times a day. In addition, the novel compounds of the present invention are useful as muscle relaxants, anticonvulsants and in the treatment of extrapyramidal disorders when indicated, at comparable dosage levels. It is understood that the exact treatment level will depend upon the case history of the animal or human individual being treated and in the last analysis the precise treatment level falling within the above guidelines is left to the discretion of the therapist.

Also included within the scope of the present invention are pharmaceutical compositions comprising the imines of this invention. Preferably these compositions are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, i.e., conventional tableting ingredients such as corn starch, lactose, sucrose, sorbitol, talc, stearic acid, magnesium stearate, dicalcium phosphate, gums, and other pharmaceutical diluents, e.g., water, to form a solid preformulation composition containing a homogeneous mixture of an imine of the present invention, or a non-toxic pharmaceutically acceptable salt, thereof. When referring to these preformulation compositions as homogeneous, it is meant that the active ingredient, is dispersed evenly throughout the composition so that the composition may be readily subdivided into equally effective unit dosage forms such as tablets, pills, capsules, and the like. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like.

The liquid forms in which the novel composition of the present invention may be incorporated for administration orally or by injection include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, gelatin and the like.

The following Examples representatively illustrate, but do not limit, the product, process, method of treatment, or compositional aspects of the present invention.

EXAMPLE 1

9,10-Dihydro-4-methyl-4H-benzo[4,5]cyclohepta[1,2-b]thiophen-4,9-imine hydrogen chloride Step A: Preparation of 4-methylene-9-(1-methyl-4-piperazinyl)-4H-benzo[4,5]cyclohepta[1,2-b]thiophene and 4-methylene-10-(1-methyl-4-piperazinyl)-4H-benzo[4,5]cyclohepta[1,2-b]thiophene To methyltriphenylphosphonium bromide (33 g) stirred in ether (680 ml) under an atmosphere of nitrogen is added dropwise 2.2 M n-butyllithium in hexane (43 ml). To the resulting mixture is added dropwise a solution of 9-(1-methyl-4-piperazinyl)- and 10-(1-methyl-4-piperazinyl)-4H-benzo[4,5]cyclohepta[1,2-b]thiophen-4-one (21 g of mixed ketoenamines) in THF (160 ml). The mixture is heated at reflux for 2 hours, then poured into ice water (700 ml). The mixture is separated and the aqueous phase is extracted with ether (2×200 ml). The combined organic fractions are washed with water (2×500 ml), dried over potassium carbonate, filtered, and evaporated to dryness in vacuo. The residue in ether (100 ml) is refrigerated and the resulting solid triphenylphosphine oxide is filtered. The filtrate is evaporated to dryness in vacuo and the residue is chromatographed on 2 kg of silica gel to provide the title compounds as a mixture. The solvent for elution is prepared by shaking methylene chloride with an equal volume of 50% (v/v) aqueous ammonia, separating and discarding the aqueous phase.

Step B: Preparation of 9-hydroximino(and 10-hydroximino-)-4-methylene-9,10-dihydro-4H-benzo-[4,5]cyclohepta[1,2-b]thiophene To a mixture of 4-methylene-9-(1-methyl-4-piperazinyl)- and 4-methylene-10-(1-methyl-4-piperazinyl)-4H-benzo[4,5]cyclohepta[1,2-b]thiophene (5 g) in methanol (80 ml) is added hydroxylamine hydrochloride (2 g) and sodium acetate (2.5 g). The mixture is heated at reflux for 1 hour, cooled, and evaporated to dryness in vacuo. The residue is treated with water (50 ml) and extracted with ether (3×50 ml). The ether layers are combined, washed with water (2×100 ml), dried over sodium sulfate, filtered, and evaporated to dryness in vacuo. The residue is chromatographed on silica gel (300 g) and eluted with methylene chloride to give 9-hydroximino- and 10-hydroximino-4-methylene-9,10-dihydro-4H-benzo-[4,5]cyclohepta[1,2-b]thiophene as separate compounds.

Step C: Preparation of 9-hydroxamino-4-methylene-9,10-dihydro-4H-benzo[4,5]cyclohepta[1,2-b]-thiophene 9-Hydroximino-4-methylene-9,10-dihydro-4H-benzo[4,5]cyclohepta[1,2-b]thiophene (5.7 g), sodium cyanoborohydride (5.4 g) and methyl orange (0.05 g) are stirred in methanol (150 ml). A solution of concentrated HCl in methanol (1:1 v/v) is added dropwise at a rate sufficient to maintain the mixture at the indicator turning point until thin layer chromatography (silica gel plate, methylene chloride elution) indicates the starting oxime has been consumed (2-3 hours). The mixture is evaporated to dryness in vacuo and the residue is treated with water (250 ml) and adjusted to pH 8 with concentrated ammonia. The mixture is extracted with ether (3×80 ml) and the combined ether layers are washed with water, dried over sodium sulfate, filtered and evaporated to dryness in vacuo to give 9-hydroxamino-4-methylene-9,10-dihydro-4H-benzo[4,5]cyclohepta-[1,2-b]thiophene.

Step D: Preparation of 9,10-dihydro-11-hydroxy-4-methyl-4H-benzo[4,5]cyclohepta[1,2-b]-thiophen-4,9-imine 9-Hydroxamino-4-methylene-9,10-dihydro-4H-benzo[4,5]cyclohepta[1,2-b]thiophene (4.5 g) and n-octane (500 ml) are combined and heated at reflux under nitrogen for 10 hours. The octane is evaporated in vacuo. The residue is treated with hexane (50 ml) and again evaporated to dryness in vacuo to give 9,10-dihydro-11-hydroxy-4-methyl-4H-benzo[4,5]cyclohepta-[1,2-b]thiophen-4,9-imine.

Step E: Preparation of 9,10-dihydro-4-methyl-4H-benzo[4,5]cyclohepta[1,2-b]thiophen-4,9-imine hydrogen chloride 9,10-Dihydro-11-hydroxy-4-methyl-4H-benzo-[4,5]cyclohepta[1,2-b]thiophen-4,9-imine (4.6 g) and zinc dust (4.2 g) are stirred in glacial and acetic acid (46 ml) maintained at 65° until thin layer chromatography (silica gel plate, 2% (v/v) methanol/chloroform elution) shows the starting hydroxy compound to be consumed (2 hours). The mixture is cooled, diluted with ice water (200 ml), and made basic with concentrated NH$_4$OH. The mixture is extracted with ether (3×80 ml) and the combined ether layers are washed with water (2×100 ml), dried over sodium sulfate, filtered, and evaporated to dryness in vacuo. The residue is chromatographed on silica gel (400 g), eluted with 1%, 1.5% and 2% (v/v) methanol in chloroform. The product fraction is evaporated to dryness in vacuo and the residue is dissolved in 95% ethanol (2 ml) and treated with a slight excess of 8 N ethanolic HCl. The solution is refrigerated, then filtered to give 9,10-dihydro-4-methyl-4H-benzo[4,5]cyclohepta[1,2-b]thiophene-4,9-imine hydrogen chloride, m.p. 324°-5°(d).

Employing the procedure substantially as described in Example 1, but using as starting materials the 9(and)10-(1-methyl-4-piperazinyl)-4H-benzo[4,5]cyclohepta[1,2-b]thiophen-4-ones and the (R$^2$)triphenylphosphonium bromides described in Table I, there are produced the 9,10-dihydro-4-R$^2$-4H-benzo[4,5]cyclohepta[1,2-b]thiophen-4,9-imines also described in Table I by the following process:

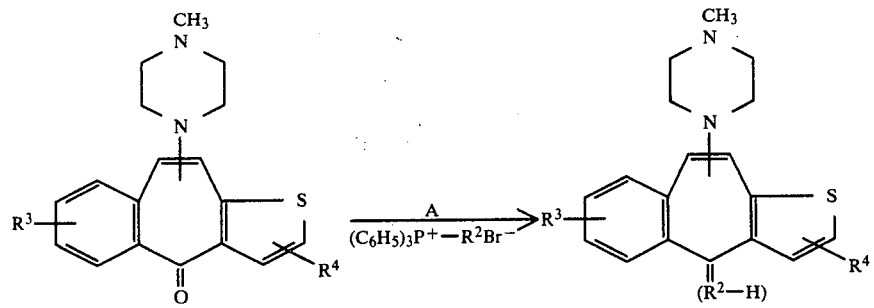

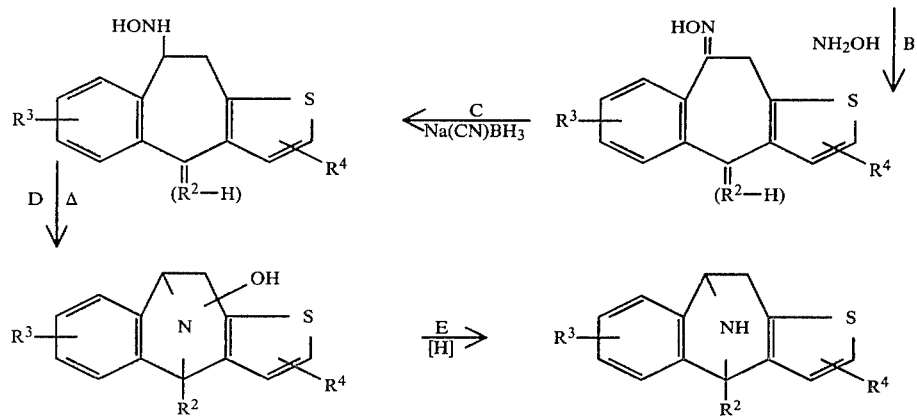

TABLE I

| R² | R³ | R⁴ |
|---|---|---|
| —C₂H₅ | H | H |
| —C₃H₇-n | H | H |
| —(CH₂)₃CH₃ | H | H |
| —CH₂C₆H₅ | H | H |
| —CH₂CH=CH₂ | H | H |
| —CH₂—⌬ | H | H |
| —(CH₂)₃N(CH₃)₂ | H | H |
| —CH₂—◁ | H | H |
| —CH₃ | 6-Br | H |
| —CH₃ | 6-F | H |
| —CH₃ | 7-Br | H |
| —CH₃ | H | 2-Br |
| —CH₃ | H | 3-Br |

EXAMPLE 3

9,10-Dihydro-4-methyl-11-benzyl-4H-benzo[4,5]cyclohepta[1,2-b]thiophene-4,9-imine fumarate 9,10-Dihydro-4-methyl-4H-benzo[4,5]cyclohepta[1,2-b]thiophene-4,9-imine (0.7 g), benzyl chloride (0.43 g), and anhydrous sodium carbonate (0.34 g) are combined in dry dimethylformamide (DMF, 18 ml) and heated at 90° under nitrogen for 10 hours. The mixture is cooled, diluted with water (35 ml) and extracted with ether (3×50 ml). The combined ether layers are washed with water (2×50 ml), dried over sodium sulfate, filtered, and evaporated to dryness in vacuo. The residue is chromatographed on silica gel (100 g) eluted with chloroform. The product fraction is evaporated to dryness in vacuo. The residue is dissolved in ethanol (5 ml) and treated with a slight excess of fumaric acid in hot ethanol (10 ml). The solution is refrigerated. The resulting solid is separated by filtration and recrystallized from ethanol to give 9,10-dihydro-4-methyl-11-benzyl-4H-benzo[4,5]cyclohepta[1,2-b]thiophene-4,9-imine fumarate, m.p. 166°-8° C.

Employing the procedure substantially as described in Example 3 but using as starting materials the -4,9-imines and alkyl halides of formula R-X, described in Table II, there are produced the 9,10-dihydro-4-R²-11-R-4H-benzo[4,5]cyclohepta[1,2-b]thiophen-4,9-imines also described in Table II by the following process:

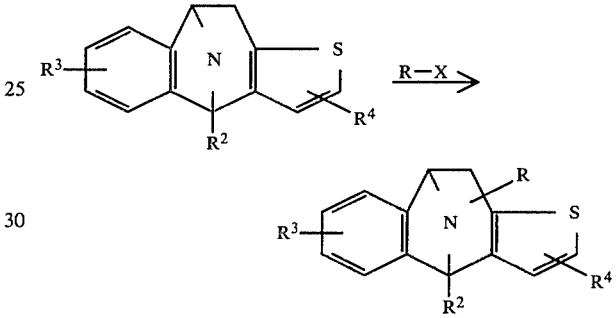

TABLE II

| R | X | R² | R³/R⁴ |
|---|---|---|---|
| —CH₃ | I | —CH₃ | H |
| —C₂H₅ | Br | —C₂H₅ | H |
| —CH₃ | I | —C₃H₇-n | H |
| —⌬ | Br | —(CH₂)₃CH₃ | H |
| —CH₂—◁ | Br | —CH₂C₆H₅ | H |
| —(CH₂)₃N(CH₃)₂ | Br | —CH₂CH=CH₂ | H |
| —CH₂C₆H₅ | Cl | —CH₂—⌬ | H |
| —CH₂C₆H₅ | Cl | —(CH₂)₃N(CH₃)₂ | H |
| —CH₂C₆H₅ | Cl | —CH₂—◁ | H |
| —CH₂C₆H₅ | Cl | —CH₃ | 6-Br |
| —CH₂CH₂CH₃ | Br | —CH₃ | 6-F |
| —CH₃ | I | —CH₃ | 7-Br |
| —CH₃ | I | —CH₃ | 2-Br |
| —CH₃ | I | —CH₃ | 3-Br |

EXAMPLE 4

9,10-Dihydro-4-methyl-11-benzyl-4H-benzo[4,5]cyclohepta[1,2-b]thiophen-4,9-imine fumarate To a solution of 9,10-dihydro-4-methyl-4H-benzo[4,5]cyclohepta[1,2-b]thiophen-4,9-imine (2.35 g) and benzaldehyde (1.1 g) in THF (100 ml) is added acetic acid (1 ml) and sodium cyanoborohydride (1.0 g). The mixture is stirred for two days, filtered and the filtrate evaporated. The residue is slurried with 1 N aqueous NH₄OH and extracted with HCCl₃. The chloroform extract is dried over sodium sulfate, filtered and evaporated. The residue is chromatographed on silica gel (100 g) eluted with chloroform. The product fraction is evaporated to dryness in vacuo. The residue is dissolved in ethanol (5 ml) and treated with a slight excess of fumaric acid in hot ethanol (10 ml). The solution is refrigerated. The resulting solid is separated by filtration and recrystallized from ethanol to give 9,10-dihydro-4-methyl-11-(benzyl)-4H-benzo-[4,5]cyclohepta[1,2-b]thiophene-4,9-imine fumarate.

EXAMPLE 5

9,10-Dihydro-4-methyl-11-ethyl-4H-benzo[4,5]cyclohepta[1,2-b]thiophen-4,9-imine fumarate An ice cold solution of 9,10-dihydro-4-methyl-4H-benzo[4,5]cyclohepta[1,2-b]thiophen-4,9-imine (2.35 g) and triethylamine (2.0 g) in ether (100 ml) is treated dropwise with acetyl chloride (1.5 g). After 10 hours, the solution is washed with water, dried over sodium sulfate, filtered, and the filtrate evaporated to dryness. The residue is redissolved in ether (200 ml) and 400 mg of LiAlH$_4$ added. The resulting slurry is stirred for 24 hours. Water is added slowly and the resulting slurry filtered. The filtrate is dried over sodium sulfate, filtered and the filtrate evaporated. The residue is chromatographed on silica gel (100 g) eluted with chloroform. The product fraction is evaporated to dryness in vacuo. The residue is dissolved in ethanol (5 ml) and treated with a slight excess of fumaric acid in hot ethanol (10 ml). The solution is refrigerated. The resulting solid is separated by filtration and recrystallized from ethanol to give 9,10-dihydro-4-methyl-11-ethyl-4H-benzo[4,5-]cyclohepta[1,2-b]-thiophene-4,9-imine fumarate.

Employing the procedure substantially as described in Example 5, but substituting for the acetyl chloride employed therein, similar molecular amounts of ethyl chloroformate or benzoyl chloride, there is produced, respectively:

9,10-dihydro-4,11-dimethyl-4H-benzo[4,5]cyclohepta[1,2-b]thiophen-4,9-imine fumarate; and 9,10-dihydro-4-methyl-11-benzyl-4H-benzo[4,5]-cyclohepta[1,2-b]thiophen-4,9-imine fumarate.

EXAMPLE 6

6-Methoxy-9,10-dihydro-4-methyl-4H-benzo[4,5]cyclohepta[1,2-b]thiophen-4,9-imine hydrogen chloride A mixture of 0.00905 mol of 6-bromo-9,10-dihydro-4-methyl-4H-benzo[4,5]cyclohepta[1,2-b]thiophen-4,9-imine, 0.181 mol of sodium methoxide, 5.56 g of electrolytic copper dust, and 87 ml of DMF is stirred and heated on a steam bath for 2.5 hours. After cooling, 150 ml of water and 150 ml of ether is added to the mixture, and, after stirring, the mixture is filtered through a pad of celite. The ether phase is separated, washed with water, dried over magnesium sulfate, filtered, and the ether is removed on a rotary evaporator. The residue is dissolved in a minimum of 95% ethanol and treated with a slight excess of 8 N ethanolic HCl. The solution is refrigerated, then filtered to give 6-methoxy-9,10-dihydro-4-methyl-4H-benzo[4,5]cyclohepta[1,2-b]thiophene-4,9-imine hydrogen chloride.

Employing the procedure substantially as described in Example 6, but using as starting materials the bromo-compounds and sodium lower alkoxides described in Table IV, there are produced the lower alkoxy-compounds also described in Table IV by the following reaction:

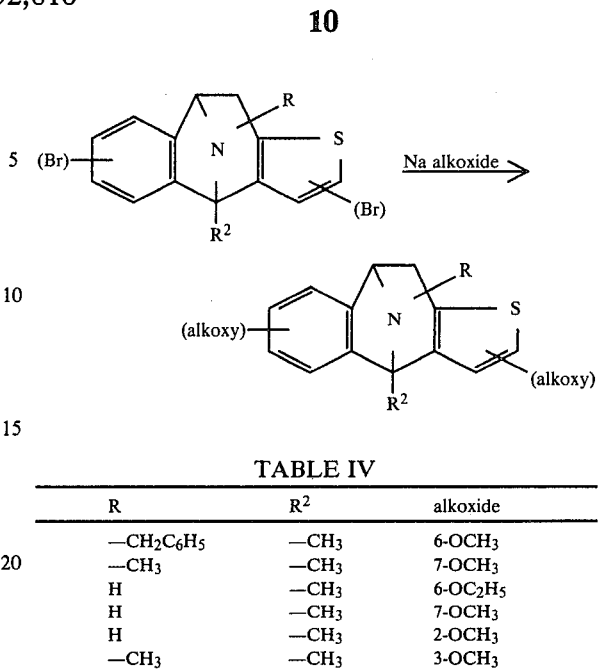

TABLE IV

| R | R$^2$ | alkoxide |
|---|---|---|
| —CH$_2$C$_6$H$_5$ | —CH$_3$ | 6-OCH$_3$ |
| —CH$_3$ | —CH$_3$ | 7-OCH$_3$ |
| H | —CH$_3$ | 6-OC$_2$H$_5$ |
| H | —CH$_3$ | 7-OCH$_3$ |
| H | —CH$_3$ | 2-OCH$_3$ |
| —CH$_3$ | —CH$_3$ | 3-OCH$_3$ |

EXAMPLE 7

6-Cyano-9,10-dihydro-4-methyl-4H-benzo[4,5]cyclohepta[1,2-b]thiophen-4,9-imine hydrogen chloride A mixture of 0.0249 mol of 6-bromo-9,10-dihydro-4-methyl-4H-benzo[4,5]cyclohepta[1,2-b]thiophen-4,9-imine, 4.58 gm (0.0498 mol) of cuprous cyanide, and 30 ml of dry dimethylformamide is stirred and heated under reflux for 6.5 hours. To the cooled solution (25° C.) is added 54 ml of water, 27 ml of a saturated aqueous solution of sodium cyanide, and 75 ml of benzene. The mixture is stirred until a two phase system is obtained. The benzene phase is removed and the aqueous phase is extracted with two 75 ml portions of benzene. The combined benzene phases are washed with 100 ml of aqueous 0.1 M sodium cyanide, three 100 ml portions of water, and dried over magnesium sulfate. After filtering, evaporation of the benzene gives a crystalline residue which is dissolved in the minimum volume of chloroform and passed over an alumina column (15"×1") packed in chloroform. The column is eluted with chloroform. Evaporation of the eluate provides a residue which is dissolved in a minimum of 95% ethanol and treated with a slight excess of 8 N ethanolic HCl. The solution is refrigerated, then filtered to give 6-cyano-9,10-dihydro-4-methyl-4H-benzo[4,5]cyclohepta[1,2-b]thiophene-4,9-imine hydrogen chloride.

Employing the procedure substantially as described in Example 7, but using as starting materials the bromo-compounds described in Table V, there are produced the cyano-compounds also described in Table V in accordance with the following reaction:

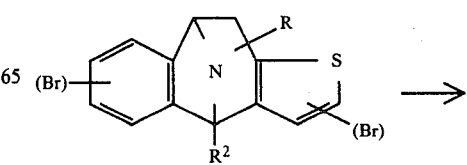

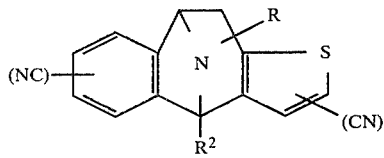

TABLE V

| R | R² | —CN Position |
|---|---|---|
| —CH₂C₆H₅ | —CH₃ | 6 |
| —CH₃ | —CH₃ | 7 |
| H | —CH₃ | 7 |
| H | —CH₃ | 2 |
| —CH₃ | —CH₃ | 3 |

EXAMPLE 8

6-Carboxy-9,10-dihydro-4-methyl-4H-benzo[4,5]cyclohepta[1,2-b]thiophen-4,9-imine hydrogen chloride A mixture of 0.00318 mol of 6-cyano-9,10-dihydro-4-methyl-4H-benzo[4,5]cyclohepta[1,2-b]thiophen-4,9-imine and 20 ml of 6 N hydrochloric acid is stirred and refluxed for 18 hours. After cooling, the mixture is filtered, and the collected solid is washed with 6 N hydrochloric acid and then with ethanol and dried to give 6-carboxy-9,10-dihydro-4-methyl-4H-benzo[4,5-]cyclohepta[1,2-b]thiophen-4,9-imine hydrogen chloride.

Employing the procedure substantially as described in Example 8, but using as starting materials the cyano-compounds described in Table VI, there are produced the carboxy-compounds also described in Table VI in accordance with the following reaction:

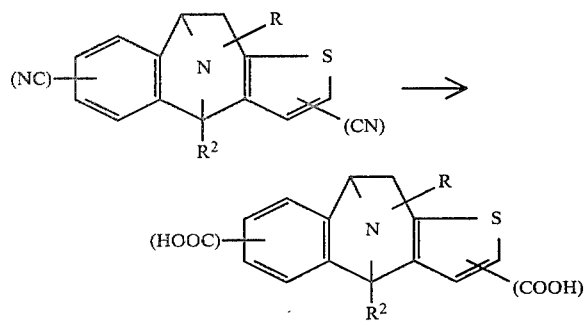

TABLE VI

| R | R² | —COOH position |
|---|---|---|
| —CH₂C₆H₅ | —CH₃ | 6 |
| —CH₃ | —CH₃ | 7 |
| —H | —CH₃ | 7 |
| —H | —CH₃ | 2 |
| —CH₃ | —CH₃ | 3 |

EXAMPLE 9

6-Trifluoromethylthio-9,10-dihydro-4-methyl-4H-benzo[4,5]cyclohepta[1,2-b]thiophen-4,9-imine hydrogen chloride A mixture of 2.24 g (0.0353 mol) of copper dust, 3.90 g (0.97 mol) of bis-(trifluoromethylthio)-mercury, (0.00484 mol) of 6-bromo-9,10-dihydro-4-methyl-4H-benzo[4,5]cyclohepta[1,2-b]thiophen-4,9-imine and 20 ml of dimethylformamide is stirred and heated under reflux for six hours. The mixture is cooled in an ice bath and 100 ml of chloroform and 30 ml of concentrated ammonium hydroxide are added. The mixture is stirred overnight at room temperature and is filtered through a pad of diatomaceous earth. The filtrate and chloroform washings are combined and separated from the aqueous phase. The chloroform phase is washed with water, dried over magnesium sulfate, filtered, and the chloroform is removed on a rotary evaporator. The residue is dissolved in 95% ethanol (2 ml) and treated with a slight excess of 8 N ethanolic HCl. The solution is refrigerated, then filtered to give 6-trifluoromethylthio-9,10-dihydro-4-methyl-4H-benzo[4,5]cyclohepta[1,2-b]thiophene-4,9-imine hydrogen chloride.

Employing the procedure substantially as described in Example 9, but using as starting materials the bromo-compounds described in Table VII, there are produced the trifluoromethylthio-compounds also described in Table VII in accordance with the following reaction:

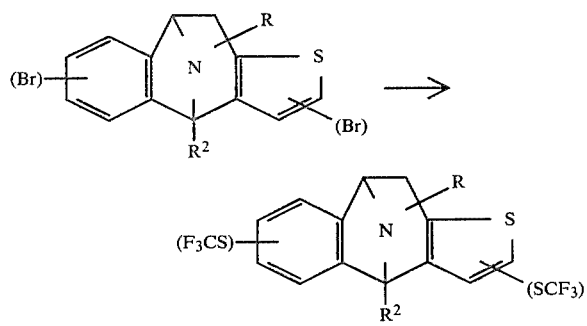

TABLE VII

| R | R² | —SCF₃ Position |
|---|---|---|
| —CH₂C₆H₅ | —CH₃ | 6 |
| —CH₃ | —CH₃ | 7 |
| —H | —CH₃ | 7 |
| —H | —CH₃ | 2 |
| —CH₃ | —CH₃ | 3 |

EXAMPLE 10

6-Hydroxy-9,10-dihydro-4-methyl-4H-benzo[4,5]cyclohepta[1,2-b]thiophen-4,9-imine hydrogen chloride A mixture of 6-methoxy-9,10-dihydro-4-methyl-4H-benzo[4,5]cyclohepta[1,2-b]thiophen-4,9-imine (2.5 g) and freshly fused pyridine hydrochloride (25 g) is heated at 210° C. for 20 minutes. The cooled mixture is slurried with water and the pH adjusted to 8.5 with concentrated ammonium hydroxide. The aqueous mixture is extracted with chloroform. The chloroform extract is washed with water, dried over Na₂SO₄, filtered and evaporated. Chromatography of the concentrate on silica gel eluted with chloroform and conversion of the product to the hydrochloride salt gives 6-hydroxy-9,10-dihydro-4-methyl-4H-benzo[4,5]cyclohepta[1,2-b]thiophen-4,9-imine hydrogen chloride.

Employing the procedure substantially as described in Example 10 but using as starting materials the alkoxy compounds described in Table VIII, there are produced the corresponding hydroxy compounds also described in Table VIII in accordance with the following reaction:

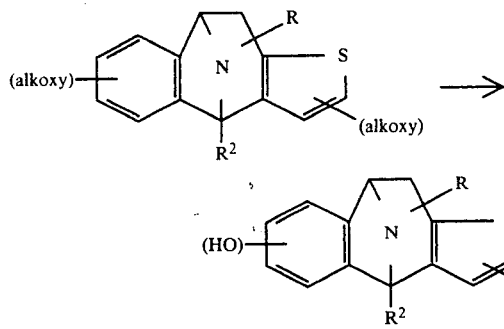

TABLE VIII

| R | R² | —OH position |
|---|---|---|
| —CH₂C₆H₅ | —CH₃ | 6 |
| —CH₃ | —CH₃ | 7 |
| H | —CH₃ | 7 |
| H | —CH₃ | 2 |
| —CH₃ | —CH₃ | 3 |

EXAMPLE 11

Preparation of intravenous solutions

A solution containing 10 mg of 9,10-dihydro-4-methyl-4H-benzo[4,5]cyclohepta[1,2-b]thiophen-4,9-imine hydrogen chloride per ml of injectable solution is prepared in the following manner.

A mixture of 10 mg of active ingredient and 9 mg of sodium chloride is dissolved in sufficient water for injection to make 1 ml of solution. The pH is adjusted using hydrochloric acid or aqueous sodium hydroxide to about pH 7.0.

If it is desired that the intravenous solution be used for multi-dose purposes, 1.0 mg of methyl-p-hydroxybenzoate (methyl paraben) and 0.10 mg of n-propyl-p-hydroxy benzoate (propyl paraben) are mixed with the other solids before adding water to dissolve the solids. The solution is prepared and stored in such a manner that it is suitably protected from the deleterious effects of the atmosphere. One method by which this can be accomplished is by preparation and storage of the solution in an atmosphere of nitrogen. The resulting solution is sterilized by autoclaving. Injectable solutions comprising 0.1, 1.0, 100.0 mg, respectively, of active ingredient per ml of solution are similarly prepared substituting the indicated amount for the above-illustrated 10 mg of quantity. Bulk injectable solutions of convenient volume for subsequent delivery in unit dosage form are readily prepared following the above procedure.

Following the above procedure, other representative injectable solutions of the present invention are prepared when 9,10-dihydro-4-methyl-4H-benzo[4,5]cyclohepta[1,2-b]thiophen-4,9-imine hydrogen chloride is replaced by an equivalent amount of any of the novel compounds of the present invention.

EXAMPLE 12

Tablet Preparation

Tablets containing 1.0, 2.0, 25.0, 26.0, 50.0, and 100.0 mg, respectively, of 9,10-dihydro-4-methyl-4H-benzo[4,5]cyclohepta[1,2-b]thiophen-4,9-imine hydrogen chloride are prepared as illustrated below.

| TABLE FOR DOSES CONTAINING FROM 1-25 MG OF THE ACTIVE COMPOUND | | | |
|---|---|---|---|
| | Amount - mg | | |
| 9,10-dihydro-4-methyl-4H-benzo[4,5]cyclohepta[1,2-b]-thiophen-4,9-imine hydrogen chloride | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount - mg | | |
| 9,10-dihydro-4-methyl-4H-benzo[4,5]cyclohepta[1,2-b]-thiophen-4,9-imine hydrogen chloride | 26.0 | 50.0 | 100.0 |
| Microcrystalline cellulose | 25.0 | 100.0 | 200.0 |
| Modified food corn starch | 2.21 | 4.25 | 8.5 |
| Magnesium stearate | .39 | 0.75 | 1.5 |

All of the active compound, lactose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg, and 100.0 mg of active ingredient per tablet. Other tablets are prepared using the same procedures and the equivalent amounts of excipients along with equivalent amounts of any of the novel compounds of the present invention.

What is claimed is:

1. A compound of structural formula:

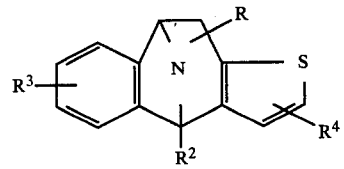

or a pharmaceutically acceptable salt thereof wherein
R is
(1) hydrogen,
(2) lower alkyl,
(3) lower alkenyl,
(4) phenyl-lower alkyl,
(5) halophenyl-lower alkyl,
(6) loweralkylphenyl-lower alkyl,
(7) lower cycloalkyl,
(8) lower (cycloalkyl-alkyl), or
(9) di(lower alkyl)amino-lower alkyl;
R² is
(1) hydrogen,
(2) lower alkyl,
(3) lower alkenyl,
(4) phenyl-lower alkyl,
(5) lower(cycloalkyl-alkyl), or
(6) di(lower alkyl)amino-lower alkyl; and
R³ and R⁴ are independently
(1) hydrogen,
(2) halogen,
(3) lower alkoxy,
(4) trifluoromethylthio, (5) cyano,
(6) carboxy, or
(7) hydroxy.

2. The compound of claim 1 wherein $R^3$ and $R^4$ are hydrogen.

3. The compound of claim 1 wherein $R^3$ and $R^4$ are hydrogen; R is hydrogen, lower alkyl or benzyl; and $R^2$ is lower alkyl.

4. A pharmaceutical antianxiety, muscle relaxant, and antiparkinson composition comprising a pharmaceutical carrier and an effective antianxiety, muscle relaxant, and antiparkinson amount of a compound of structural formula:

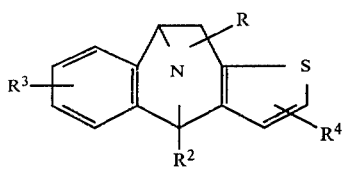

or a pharmaceutically acceptable salt thereof wherein
R is
  (1) hydrogen,
  (2) lower alkyl,
  (3) lower alkenyl,
  (4) phenyl-lower alkyl,
  (5) halophenyl-lower alkyl,
  (6) loweralkylphenyl-lower alkyl,
  (7) lower cycloalkyl,
  (8) lower(cycloalkyl-alkyl), or
  (9) di(lower alkyl)amino-lower alkyl;
$R^2$ is
  (1) hydrogen,
  (2) lower alkyl,
  (3) lower alkenyl,
  (4) phenyl-lower alkyl,
  (5) lower(cycloalkyl-alkyl), or
  (6) di(lower alkyl)amino-lower alkyl; and
$R^3$ and $R^4$ are independently
  (1) hydrogen,
  (2) halogen,
  (3) lower alkoxy,
  (4) trifluoromethylthio,
  (5) cyano,
  (6) carboxy, or
  (7) hydroxy.

5. The composition of claim 4 wherein $R^3$ and $R^4$ are hydrogen.

6. The composition of claim 4 wherein $R^3$ and $R^4$ are hydrogen; R is hydrogen, lower alkyl or benzyl; and $R^2$ is lower alkyl.

7. A method of treating anxiety which comprises the administration to a patient in need of such treatment an effective amount of a compound of structural formula:

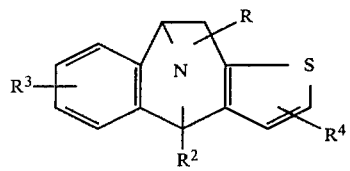

or a pharmaceutically acceptable salt thereof wherein
R is
  (1) hydrogen,
  (2) lower alkyl,
  (3) lower alkenyl,
  (4) phenyl-lower alkyl,
  (5) halophenyl-lower alkyl,
  (6) lower alkylphenyl-lower alkyl,
  (7) lower cycloalkyl,
  (8) lower(cycloalkyl-alkyl), or
  (9) di(lower alkyl)amino-lower alkyl;
$R^2$ is
  (1) hydrogen,
  (2) lower alkyl,
  (3) lower alkenyl,
  (4) phenyl-lower alkyl,
  (5) lower(cycloalkyl-alkly), or
  (6) di(lower alkyl)amino-lower alkyl; and
$R^3$ and $R^4$ are independently
  (1) hydrogen,
  (2) halogen,
  (3) lower alkoxy,
  (4) trifluoromethylthio,
  (5) cyano,
  (6) carboxy, or
  (7) hydroxy.

8. The method of claim 7 wherein $R^3$ and $R^4$ are hydrogen.

9. The method of claim 7 wherein $R^3$ and $R^4$ are hydrogen; R is hydrogen, lower alkyl or benzyl; and $R^2$ is lower alkyl.

* * * * *